United States Patent [19]

Cho

[11] 4,430,340

[45] Feb. 7, 1984

[54] STABILIZATION OF PGI$_2$ COMPOUNDS WITH SURFACTANTS

[75] Inventor: Moo J. Cho, Kalamazoo, Mich.

[73] Assignee: The Upjohn Company, Kalamazoo, Mich.

[21] Appl. No.: 925,013

[22] Filed: Jul. 17, 1978

[51] Int. Cl.$^3$ .............................................. A61K 31/34
[52] U.S. Cl. ..................................................... 424/285
[58] Field of Search ........................................ 424/285

[56] References Cited

U.S. PATENT DOCUMENTS

| | | | |
|---|---|---|---|
| 3,851,052 | 11/1974 | Monkhouse | 424/318 |
| 3,882,241 | 5/1975 | Pharriss | 424/318 |
| 3,899,587 | 8/1975 | Pharriss | 424/318 |
| 3,903,297 | 9/1975 | Robert | 424/318 |

OTHER PUBLICATIONS

Moncada et al., Nature, vol. 263, Oct. 21, 1976, pp. 663-665.

*Primary Examiner*—Jerome D. Goldberg
*Attorney, Agent, or Firm*—Robert A. Armitage; Lawrence T. Welch

[57] ABSTRACT

The present invention provides novel methods for the stabilization of aqueous solutions of prostacyclin and related prostacyclin analogs comprising the addition of neutral or cationic surfactants to such aqueous solutions. Additionally, the novel surfactant-containing solutions of prostacyclin and related compounds are described. Finally there are provided novel pharmaceutical compositions comprising surfactant-containing aqueous solutions of prostacyclin and related compounds.

1 Claim, No Drawings

STABILIZATION OF PGI₂ COMPOUNDS WITH SURFACTANTS

BACKGROUND OF THE INVENTION

1. Field of the Invention

The present invention relates to novel stabilized solutions and pharmaceutical compositions. The invention further relates to novel methods for stabilizing known pharmaceutical compositions.

In particular, the invention relates to stable pharmaceutical compositions of enol ether-containing prostacyclins. Further, the invention particularly relates to methods for stabilizing pharmaceutical compositions containing such prostacyclins.

Prostacyclin is an endogenously produced compound in mammalian species, being structurally and biosynthetically related to the prostaglandins (PG's). In particular, prostacyclin exhibits the following structure and carbon numbering:

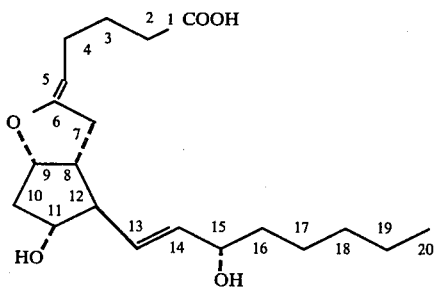

5,6-Dihydroprostacyclin exhibits the following structure and carbon numbering:

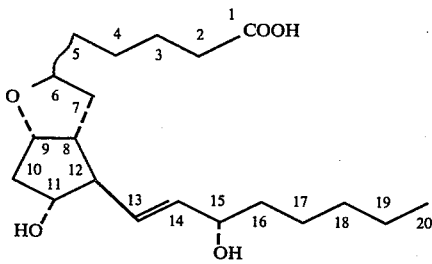

As is apparent from inspection of formulas I and II, prostacyclin and 5,6-dihydroprostacyclin (i.e., PGI₁) bear a structural relationship to PGF₂α, which exhibits the following structure and carbon numbering:

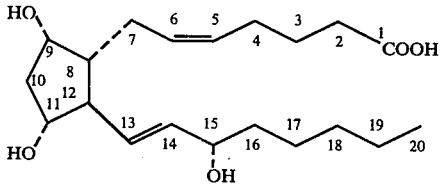

As is apparent by reference to formula III, prostacyclin and 5,6-dihydroprostacyclin may be trivially named as a derivative of PGF-type compounds. Accordingly, prostacyclin is trivially named 9-deoxy-6,9α-epoxy-(5Z)-5,6-didehydro-PGF₁ and 5,6-dihydro prostacyclin is named 9-deoxy-6,9α-epoxy-PGF₁. For description of the geometric stereoisomerism employed above, see Blackwood et al., Journal of the American Chemical Society 90, 509 (1968). Further, for a description of prostacyclin and its structural identification, see Johnson et al., Prostaglandins 12, 915 (1976).

When referred to herein, prostacyclin analogs will be referred to herein, prostacyclin analogs will be referred to by trivial, art-recognized system of nomenclature described by N. A. Nelson, Journal of Medicinal Chemistry, 17, 911 (1974) for the prostaglandins. Accordingly, all of the prostacyclin derivatives herein will be named as 9-deoxy-PGF₁-type compounds or alternatively and preferably as PGI₁ or PGI₂ derivatives.

Among the known analogs of prostacyclin or PGI₂ are compounds wherein modifications are introduced into the C-12 side chain, the non-heterocyclic cyclopentane ring is optionally substituted or unsubstituted, or the carboxy-terminated side chain exhibits varying substituents on the C-4 to C-2 position. Such analogs of prostacyclin are described in U.S. Ser. No. 819,940, filed July 28, 1977.

Another class of prostacyclin analogs includes those which are epimeric to prostacyclin with respect to the C-5 unsaturation, and optionally contain other modifications as referred to in the preceding paragraph. Such analogs of prostacyclin are typified by (5E)-PGI₂, a compound of the following formula:

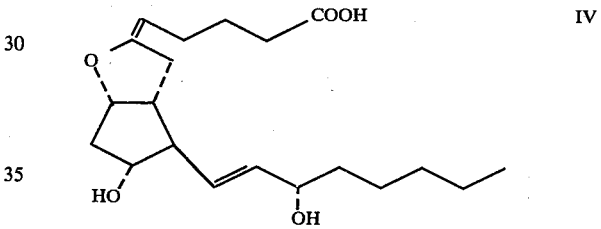

Such geometric isomers of prostacyclin are described in U.S. Ser. No. 775,003, filed Mar. 7, 1977.

Also known among the analogs of prostacyclin are compounds containing a 6-membered heterocyclic ring (instead of the 5-membered heterocyclic ring of prostacyclin) and optionally containing the various other analog features above. Such compounds are described in U.S. Ser. No. 819,856, filed July 28, 1977, and are typified by 9-deoxy-5,6α-epoxy-(4Z)-4,5-didehydro-PGF₁, a prostacyclin analog of the following formula:

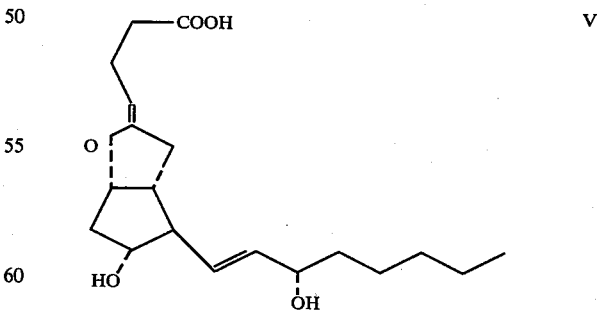

Yet another class of prostacyclin analogs is that wherein the 5-6 unsaturation of prostacyclin is isomerized to the 6,7-position. Such compounds, described in U.S. Ser. No. 860,673, filed Dec. 15, 1977, are typified by 6,7-didehydro-PGI₁, a prostacyclin analog of the following formula:

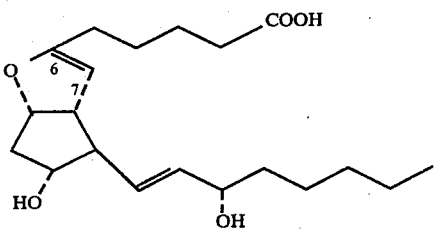

VI

Each of the foregoing prostacyclin analogs, except 5,6-dihydro prostacyclin (PGI$_1$), is an enol-ether, which is relatively unstable in aqueous solutions. As is known in the art, enol ethers typically hydrolyze in aqueous solutions, an effect which may severely limit the time interval between the preparation of such an aqueous solution and its subsequent use, e.g., for intravenous infusion. For example, in neutral and acidic solutions, prostacyclin is known to rapidly hydrolyze to 6-keto-PGF$_1\alpha$. See the paper of M. J. Cho and M. A. Allen in Prostaglandins (1978), and various references cited therein.

Notwithstanding the relative instability of prostacyclin and related analogs in solution, pharmaceutical compositions for parenteral administration of these compounds are known in the art and are known to be useful in the induction of prostacyclin - like pharmacological effects. See particularly the various U.S. patent application referred to above, the relevant disclosure of which with respect to compositions and methods for parenteral administration of these compounds is incorporated herein by reference.

There are further known in the art surfactants exhibiting a wide range of structural variation. Surfactants are known in the art and defined in the art to be surface-active organic compounds, which are capable of modifying the surface tension of aqueous solutions in which they are present. A determination of whether an organic compound is indeed a surfactant is readily assessed by the effect of that compound on the surface tension of an aqueous solution by methods known in the art. See for example Rowe, E. L., "Automated Drop Volume Apparatus for Surface Tension Measurement", J. Pharm. Sci., 61:781–782 (1972).

While a wide variety of surfactants is known in the art, including detergents and the like, a more limited variety of surface-active agents have potential utility in pharmaceutical preparations. Among these are the various surfactants described by Charnicki, W. F., Am. J. Pharm. 409 (1958); Mulley, V. A., et al., Adv. Pharm. Sci. 1:87 (1964); and, Mukerjee, P., et al., "Critical Micelle Concentrations of Aqueous Surfactant Systems", U.S. Government Printing Office, Washington, D.C., 1971.

The various surfactants known in the art exhibit a concentration dependent modification of surface tension when in aqueous solution. Typically, surface tension will decrease as the concentration of surfactant increases, until a "critical micellar concentration" (CMC) is reached. Increasing the concentration of surfactant beyond the CMC typically causes no further reduction in surface tension.

Accordingly, for any surfactant, the CMC is readily determined by measuring the surface tension (e.g., the method of Rowe, cited above) and determining the lowest concentration at which the marginal change in surface tension is zero.

Finally, numerous categories of surfactants are known in the art. Typically, surfactants are categorized by whether or not they contain ionic functional groups. Accordingly, there are known both neutral and ionic surfactants and ionic surfactants are further categorized as being either cationic or anionic. As the same suggests, cationic surfactants contain at least one electron-deficient (positively charged) functional group, while anionic surfactants contain at least one electron-enriched (negatively charged) functional group. Otherwise, surfactants are typically characterized by relatively long chained carbon backbones, providing a hydrophobic region.

Prior Art

Numerous methods for the stabilization of relatively unstable prostaglandins are known in the art. For example, the use of cyclodextrin clathrates for the stabilization of prostaglandins is described in Belgian Pat. No. 768,288 (Derwent Farmdoc CPI No. 80084S-B). Further, the stabilization of PGE$_2$ (Prostaglandin E$_2$) in anhydrous alcohol is described in U.S. Pat. No. 3,749,800, while the stabilization of PGE$_2$ in polar, aprotic solvents is described in U.S. Pat. No. 3,829,579. Further, the use of surfactants to prevent the C-15 epimerization of 15-methyl-PGF$_2\alpha$ is reported in Allen, M. A., "The Effects of Surfactants on the Epimerization of 15(S) 15-methyl-PGF$_2\alpha$", a B.A. dissertaion submitted to Kalamazoo College, Kalamazoo, Mich. in 1977.

Further, the use of surfactants to catalyze or inhibit chemical reactions is known in the art. Discussions of the catalytic effects of surfactants on chemical reactions is described in Tanford, C., "The Hydrophobic Effect Formation of Micelles and Biological Membranes", Wiley and Sons, New York, N.Y., 1973; Bunton, C. A., Prog. Sol. St. Chem. 8:239 (1973); Cordes, B., "Reactions Kinetics in Micelles", Plenum Press, New York, N.Y., 1973; Fendler, J. H., et al., "Catalysis in Micellar and Macromolecular Systems", Academic Press, New York, N.Y., 1975; Piszkiewicz, D., Journal of Am. Chem. Soc. 99:1550 (1977); and, Dougherty, S. J., et al., "On the Prediction of Reaction Rate in Micellar Solutions", J. Coll. Int. Sci., 49:135–138 (1974).

Regarding the inhibition of chemical reactions in surfactant-containing aqueous solutions, see Bunton, C. A., "Micellar Catalysis and Inhibition", Progress in Solid-State Chemistry, Vol., 8; McCaldin, J. O., Ed., Pergamon Press, New York, N.Y. (pp 239–281); and, Mitchell, A. G., "The Hydrolysis of Propylbenzoate in Aqueous Solutions of Cetomacrogol", J. Pharm. Pharmacol., 15:761–765 (1963); and, Cho, M. J., et al, "Quantative Assessment of the Negative Catalytic Effects of a Cationic Surfactant Myristyl-$\gamma$-Picolinium Chloride on the Specific-Acid Catalyzed Epimerization of 15(S) 15-methyl PGF$_2\alpha$", in the June, 1978, issue of Intl. J. Pharm.

SUMMARY OF THE INVENTION

The present invention provides novel stabilized aqueous solutions and pharmaceutical compositions. Further, the present invention provides novel methods for stabilizing pharmaceutical agents in aqueous solutions.

In particular, the present invention relates to novel aqueous solutions of enol-ether prostacyclins and pharmaceutical compositions comprising such stable aqueous solutions. Also, the invention particularly provides methods for stabilization of aqueous solutions containing enol-ether prostacyclins. More especially, the present invention provides:

(a) In an aqueous solution of an enol-ether prostacyclin, the improvement which comprises:
a pharmaco-stabilizing surfactant at a stabilizing, pharmaceutically acceptable concentration;

(b) A pharmaceutical composition, suitable for parenteral administration, which comprises:
(1) a quantity of water;
(2) an amount of a pharmaco-stabilizing surfactant; which, when mixed with said quantity of water, is present therein in a stabilizing, pharmaceutically acceptable concentration; and
(3) an amount of an enol-ether prostacyclin; which, when mixed with said quantity of water, is present therein at a concentration acceptable for pharmaceutical administration;

(c) In a method for preparing an aqueous solution containing an enol-ether prostacyclin, the improvement which comprises:
adding to said aqueous solution a pharmaco-stabilizing surfactant in an amount such that a stabilizing, pharmaceutically acceptable concentration is present therein; and (d) In a method for preparing an aqueous pharmaceutical composition of an enol-ether prostacyclin, suitable for parenteral administration, the improvement which comprises:
adding to said pharmaceutical composition an amount of a pharmaco-stabilizing surfactant such that there is present therein a stabilizing, pharmaceutically acceptable concentration of said neutral or cationic surfactant.

The term "enol-ether prostacyclin" refers to not only prostacyclin itself, but any of the various analogs thereof which exhibit the enol-ether functionality.

Further, conventional aquous solutions of such enol-ether prostacyclins are described in the aforementioned references describing the enol-ether prostaglandins. Particularly being described are those aqueous solutions representing suitable pharmaceutical compositions for parenteral administration. For example, such conventional pharmaceutical compositions suitable for parenteral administration are those formulated with a pH varying from 4.0 to 10.0, preferably those being essentially isotonic with the intended host.

Such conventional aqueous pharmaceutical compositions include not only the enol-ether prostacyclin (e.g., in its free acid, salt, ester, or amide form for the carboxy-containing enol-ether prostacyclins), but sodium chloride, buffers, preservatives, and other additives required to achieve and maintain the pharmaceutical acceptability and elegance of the formulation.

Formulations thusly prepared are those intended for any of the known parenteral routes of administration for the enol-ether prostacyclins. Particularly, intravenous intramuscular, intraamniotic, extraamniotic, and intra-arterial routes of administration fall within the ambit of those parenteral routes of administration for which conventional aqueous pharmaceutical compositions are prepared.

The pharmaco-stabilizing surfactants are any relatively non-toxic, neutral or cationic surfactants exhibiting a stabilizing, pharmaceutically acceptable concentration. For example, when a pharmaceutical composition is considered, a pharmaceutically acceptable concentration of the surfactant is any concentration less than the concentration at which the surfactant exhibits toxic or other ontoward effects on the hose to whom the composition is being administered. Ordinarily, the concentration of surfactant must be less than about 0.3 M, and preferably less than 0.01 M for pharmaceutical acceptability.

A stabilizing concentration of surfactant is any concentration of surfactant greater than the critical micellar concentration (CMC) of that surfactant. The CMC for a given surfactant is determined by methods known in the art, by reference to standard techniques. See in particular the references cited above.

The surfactants used in connection with the present invention are only to those surfactants for which the minimum stabilizing concentration is less than the maximum pharmaceutically acceptable concentration. Thus, as used in connection with the present invention, the useful surfactants are only those chemical entities which are relatively non-toxic such that the use of such agents in a pharmaceutical composition would be acceptable.

Cationic surfactants in accordance with the present invention are particularly compounds containing a long carbon atom chain ($C_8$ to $C_{25}$) together with a basic nitrogen atom, where, for example, the halide salt thereof would yield a cationic form of the nitrogen.

Such surfactants also typically have an aromatic structural component, for example, a benzene ring or a hetero ring, e.g., where nitrogen represents the hetero atom. Hence, these cationic surfactants include the dialkyl(alkylbenzyl) ammonium halides, e.g., dimethyl(hexadecylbenzyl) ammonium chloride, and alkylpyridyl halides (e.g., myristyl-γ-picolinium chloride, hexadecylpyridinium chloride, and an octadecylpyridinium chloride). However non-aromatic surfactants include trialkylammonium halides, e.g., hexadecyltrimethylammonium chloride. The cationic surfactants employed in accordance with the present invention are readily available from commercial sources or are alternatively prepared by known methods or analogously to such known methods.

For the neutral surfactants in accordance with the present invention, there are included the polysorbates (e.g., polysorbate 20, polysorbate 60, and polysorbate 80), polyethylene glycols (molecular weight 1500 to 2500), lethicins, propylene glycol and ethylene glycol copolymers, and polyoxyethylated vegetable oils. These compounds are known in the art or prepared by methods readily known in the art. For example, the polyethylene glycols are known or prepared by available polymerization methods.

For more extensive lists of pharmaceutically acceptable surfactants, see the references cited above.

Finally with regard to the improved aqueous solutions of the enol-ether prostacyclins in accordance with the present invention, there are particularly contemplated such aqueous solutions containing the enol-ether prostacyclin at a concentration substantially greater than that intended for the enol-ether prostacyclin in a corresponding pharmaceutical composition. Such improved aqueous solutions are in particular useful in preparing pharmaceutical compositions therefrom by dilution of the concentrated aqueous solution with a parenterally acceptable diluent (e.g., aqueous dextrose or physiological saline). For example, an aqueous solution containing 50–100 μg/ml of prostacyclin sodium salt is prepared with a stabilizing concentration of the pharmaco-stabilizing surfactant. Thereafter, dilution with physiological saline at the time of or immediately prior to parenteral administration yields a pharmaceutical composition of prostacyclin of between 5.0 and 0.5 µg/ml.

DESCRIPTION OF THE PREFERRED EMBODIMENTS

EXAMPLE 1

A pharmaceutical composition in accordance with the present invention suitable for intravenous injection is prepared by conventional techniques from the following constituents:

| | | |
|---|---|---|
| Sodium Salt of PGI$_2$ | 10.0 | mg |
| NaCl USP | 9.0 | gm |
| Benzyl Alcohol USP | 9.0 | gm |
| Benzalkonium Chloride USP | 5.0 | gm |
| NaH$_2$PO$_4$.H$_2$O ACS Grade | 0.69 | gm |
| Na$_2$HPO$_4$.7H$_2$O ACS Grade | 13.40 | gm |
| Water for Injection USP | q.s. to 1.01 | |

The above solution of prostacyclin at 10 µg/ml concentration may be stored for prolonged periods and is thereafter diluted to 1.0 µg/ml by addition of 9 volumes of physiological saline; then immediately used for intravenous infusion (1 ml/min).

Benzalkonium chloride refers to commercially available mixtures of alkylbenzyldimethylammonium chlorides of from 8 to 18 carbon atoms in the alkyl chain, or such mixtures prepared by known methods. See Merck Index, Ninth Edition, p. 137 (1976).

EXAMPLE 2

In accordance with Example 1, but substituting polysorbate 20 USP in place of benzalkonium chloride USP, there is prepared a neutral surfactant-containing composition in accordance with the present invention.

What is claimed is:

1. A pharmaceutical composition, suitable for parenteral administration, which comprises:
   (1) a quantity of water;
   (2) an amount of hexodecyltrimethylammonium chloride (CTAC); which, when mixed with said quantity of water, is present therein in a stabilizing, pharmaceutically acceptable concentration; and
   (3) an amount of prostacyclin sodium salt; which, when mixed with said quantity of water, is present therein at a concentration acceptable for pharmaceutical administration.

* * * * *

UNITED STATES PATENT OFFICE
CERTIFICATE OF CORRECTION

Patent No. 4,430,340              Dated  7 February 1984

Inventor(s) M.J. Cho

It is certified that error appears in the above-identified patent and that said Letters Patent are hereby corrected as shown below:

Column 2, lines 55-58, that portion of the formula should appear as follows:

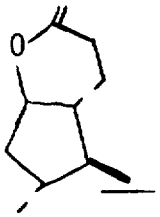

Column 3, lines 7-10, that portion of the formula should appear as follows:

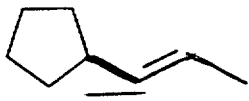

Column 4, line 8, "the same" should read -- the name --.
Column 4, line 29, "dissertaion" should read -- dissertation --.
Column 4, lines 37-8, ""Reactions" should read -- "Reaction --.

Signed and Sealed this

Twenty-third Day of October 1984

[SEAL]

Attest:

GERALD J. MOSSINGHOFF

Attesting Officer    Commissioner of Patents and Trademarks